(12) United States Patent
Wang et al.

(10) Patent No.: US 11,380,189 B2
(45) Date of Patent: Jul. 5, 2022

(54) URINE DETECTION METHOD AND URINE DETECTION DEVICE

(71) Applicants: ASTEK TECHNOLOGY LTD., Tainan (TW); CHIMEI MEDICAL CENTER, Tainan (TW)

(72) Inventors: Jhi-Joung Wang, Tainan (TW); Ying-Li Lee, Tainan (TW); Jiun-Hung Lin, Tainan (TW); Chun-Hao Lu, Tainan (TW); Yu-Tung Lu, Tainan (TW); Yen-Jung Lu, Tainan (TW)

(73) Assignees: Astek Technology Ltd., Tainan (TW); Chimei Medical Center, Tainan (TW)

( * ) Notice: Subject to any disclaimer, the term of this patent is extended or adjusted under 35 U.S.C. 154(b) by 0 days.

(21) Appl. No.: 17/197,439

(22) Filed: Mar. 10, 2021

(65) Prior Publication Data

US 2022/0068112 A1 Mar. 3, 2022

(30) Foreign Application Priority Data

Sep. 1, 2020 (TW) .................................. 109129857

(51) Int. Cl.
*G08B 21/24* (2006.01)
*A61F 13/42* (2006.01)
*A61F 13/15* (2006.01)

(52) U.S. Cl.
CPC ............. *G08B 21/24* (2013.01); *A61F 13/42* (2013.01); *A61F 2013/15146* (2013.01); *A61F 2013/424* (2013.01)

(58) Field of Classification Search
CPC ............... G08B 21/24; A61F 13/42; A61F 2013/15146; A61F 2013/424
See application file for complete search history.

(56) References Cited

U.S. PATENT DOCUMENTS

| | | | |
|---|---|---|---|
| 7,221,279 B2* | 5/2007 | Nielsen | A61F 13/42 |
| | | | 340/384.1 |
| 10,561,541 B1* | 2/2020 | Heyl | A61F 13/42 |
| 2004/0147888 A1* | 7/2004 | Huang | A61F 13/42 |
| | | | 604/361 |
| 2008/0278337 A1 | 11/2008 | Huang et al. | |

FOREIGN PATENT DOCUMENTS

| | | |
|---|---|---|
| TW | I327063 B | 7/2010 |
| TW | M511841 U | 11/2015 |

\* cited by examiner

*Primary Examiner* — Nabil H Syed
*Assistant Examiner* — Cal J Eustaquio
(74) *Attorney, Agent, or Firm* — Rosenberg, Klein & Lee

(57) ABSTRACT

A urine detection method and a urine detection device are disclosed. The method includes the steps of: providing a capacitive humidity detection unit to be placed on a diaper, wherein the capacitive humidity detection unit is configured to detect a humidity of the diaper to generate a capacitance value; providing a processing unit to record an environmental capacitance value, wherein when the processing unit receives the capacitance value, it compares the capacitance value with the environmental capacitance value, when the capacitance value is greater than the environmental capacitance value, the processing unit generates a reminder signal; providing a reminder unit to generate a reminder when receiving the reminder signal. The urine detection device is used for performing the urine detection method.

7 Claims, 8 Drawing Sheets

URINE DETECTION METHOD AND URINE DETECTION DEVICE

FIELD OF THE INVENTION

The present invention relates to a urine detection method and a urine detection device. A capacitance value is generated by detecting the humidity of a diaper, and the capacitance value is compared with an environmental capacitance value in the environment, so as to accurately sense whether the diaper is wet or not.

BACKGROUND OF THE INVENTION

Diapers are mainly used for those who are unable to take care of themselves, for example, infants, the elderly, patients with incontinence, and disabled persons who lose their ability to take care of themselves. The caregiver may neglect to change the diaper because he/she is not sure whether the diaper is wet or he/she is busy. When the diaper is not changed in time for a long period of time, it is possible to cause skin damages, such as bedsores, pressure ulcer, eczema, and diaper rash.

In order to solve the above-mentioned situation, Taiwan Utility Model Publication No. M590396 discloses a pad capable of sensing urine humidity, comprising a main body combined with a breathable layer; a humidity sensor for detecting a humidity value on the surface of the breathable layer and for sending a humidity signal when the humidity value exceeds a humidity standard value; a processing unit for outputting a warning signal after receiving the humidity signal; a warning unit for sending out a warning after receiving the warning signal; a transmitting unit for transmitting the warning signal to a remote handheld electronic device; and a power source electrically connected to the processing unit for supplying power required for its operation.

The humidity sensor disclosed in Taiwan Utility Model Publication No. M590396 has a large error. Although the humidity standard value reduces the error, the humidity sensor has a large sensing error and poor sensitivity, so the user is easily affected by misjudgment.

Taiwan Patent Publication No. 1327063 discloses a urine wetness sensing system and method, which is used to test the humidity in a diaper of a test subject, comprising an electrode, a capacitance sensor, and a display device. The electrode is a lithographic electrode, which includes a first electrode area and a second electrode area. The capacitance sensor includes a first sensing electrode and a second sensing electrode. The first sensing electrode and the first electrode area form a first sensing capacitor. The second sensing electrode and the second electrode area form a second sensing capacitor. A processor detects the capacitance values of the first sensing capacitor and the second sensing capacitor and determines a humidity signal according to changes in the capacitance values of the first sensing capacitor and the second sensing capacitor. The display device receives the humidity signal and displays the humidity value corresponding to the humidity signal.

As disclosure in Taiwan Patent Publication No. 1327063, the first sensing electrode and the second sensing electrode detect the humidity on both sides of the diaper, but the inner part may contact the user and cause discomfort, and the manufacturing cost is relatively high.

SUMMARY OF THE INVENTION

In view of the above-mentioned shortcomings of the conventional urine detection method and device, the present invention provides a urine detection method, comprising the steps of:

providing a capacitive humidity detection unit to be placed on a diaper, wherein the capacitive humidity detection unit is configured to detect a humidity of the diaper to generate a capacitance value;

providing a processing unit to record an environmental capacitance value, wherein when the processing unit receives the capacitance value, the processing unit compares the capacitance value with the environmental capacitance value, when the capacitance value is greater than the environmental capacitance value, the processing unit generates a reminder signal;

providing a reminder unit to generate a reminder when receiving the reminder signal.

Preferably, the urine detection method further provides a wireless transmission element for receiving the reminder.

The present invention further provides a urine detection device, attached to a diaper to be put on a human body. The urine detection device comprises a main body. The main body includes a capacitive humidity detection unit, a processing unit, and a reminder unit. The capacitive humidity detection unit has a sensing electrode. When the main body is attached to the diaper, the sensing electrode forms a capacitance value with the human body. The processing unit is disposed on the main body. The processing unit is connected to the capacitive humidity detection unit and configured to record an environmental capacitance value. When the processing unit receives the capacitance value, the processing unit compares the capacitance value with the environmental capacitance value. When the capacitance value is greater than the environmental capacitance value, the processing unit generates a reminder signal. The reminder unit is disposed on the main body. The reminder unit is connected to the processing unit. When the reminder unit receives the reminder signal, the reminder unit generates a reminder.

Preferably, the urine detection device further comprises a wireless transmission element disposed on the main body. The wireless transmission element is connected to the reminder unit. The wireless transmission element is configured to receive the reminder.

Preferably, the wireless transmission element is any one of a Bluetooth, a wireless network WI-FI, a near field communication NFC and a radio frequency identification RFID.

Preferably, the main body includes a rechargeable battery module. The rechargeable battery module is connected to the capacitive humidity detection unit, the processing unit, and the reminder unit.

Preferably, the urine detection device further comprises an adhesive. The main body is adhered to the diaper with the adhesive. The adhesive is an aquogel or a double-sided tape.

The above technical features have the following advantages:

1. The present invention detects the humidity of the diaper through the capacitive humidity detection unit to generate the capacitance value, and compares it with the environmental capacitance value preset by the processing unit. When the capacitance value is greater than the environmental capacitance value, the reminder unit generates a reminder. The capacitive humidity detection unit that senses humidity by means of the capacitance change has high sensitivity, good product interchangeability, fast response speed and low humidity hysteresis, and is easy to manufacture, easy to achieve miniaturization and integration, and can detect the humidity quickly. Furthermore, through the preset environmental capacitance value, it is able to avoid the misjudgment caused by the interference of environmental changes.

2. When the wireless transmission element of the present invention receives the reminder, it can transmit the reminder to a mobile phone or tablet to remind the caregiver through the wireless transmission element.

3. With the rechargeable battery module, the urine detection device of the present invention does not need to replace the battery. It can be charged and used repeatedly.

DESCRIPTION OF THE PREFERRED EMBODIMENTS

Embodiments of the present invention will now be described, by way of example only, with reference to the accompanying drawings.

Figure 1:
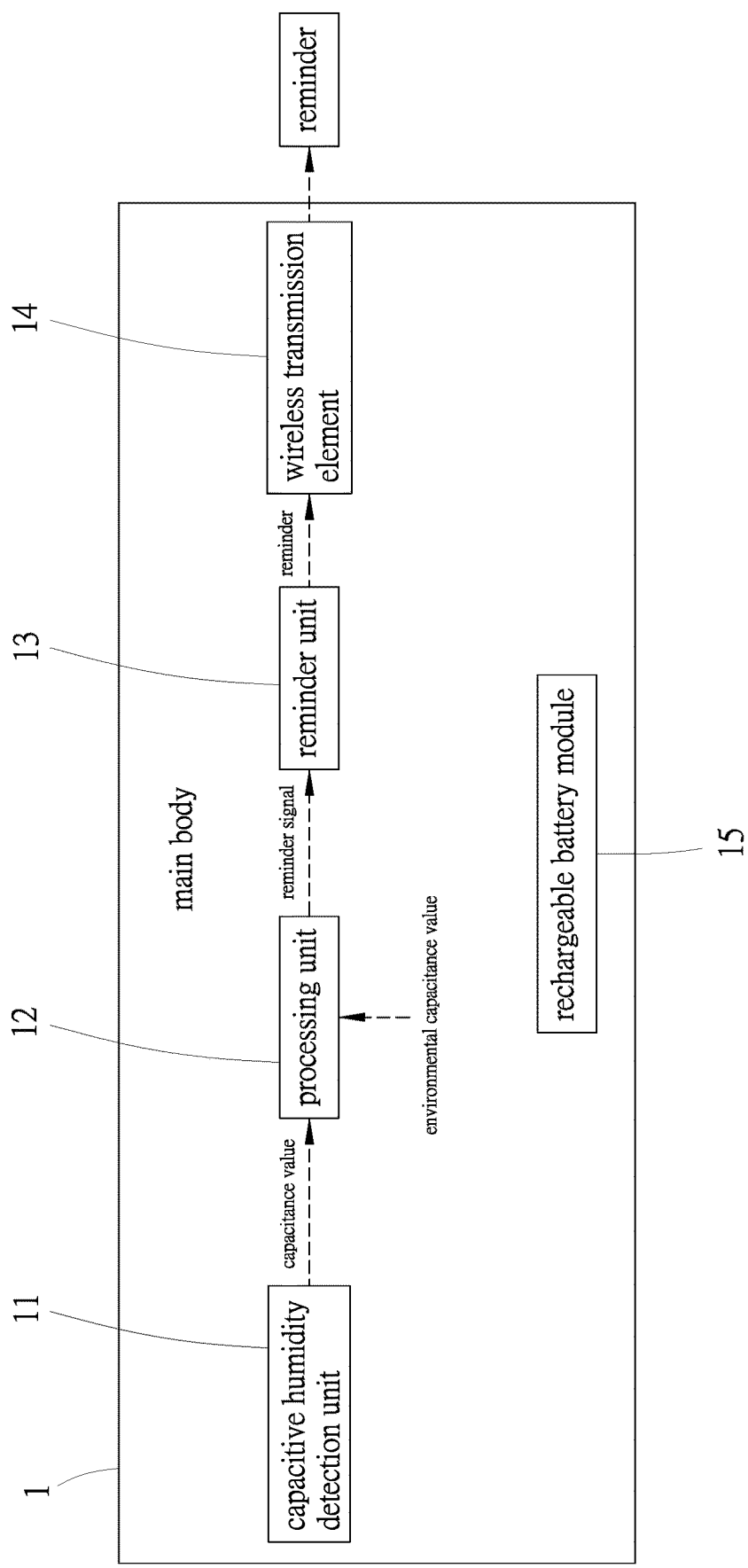
FIG. 1 is a block diagram of the urine detection device of the present invention.
Figure 2:
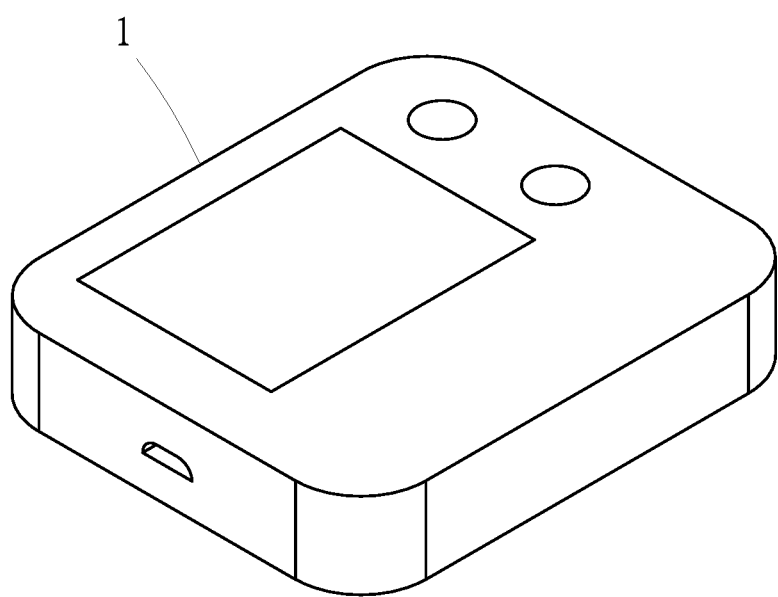
FIG. 2 is a perspective view of the urine detection device of the present invention.
Figure 3:
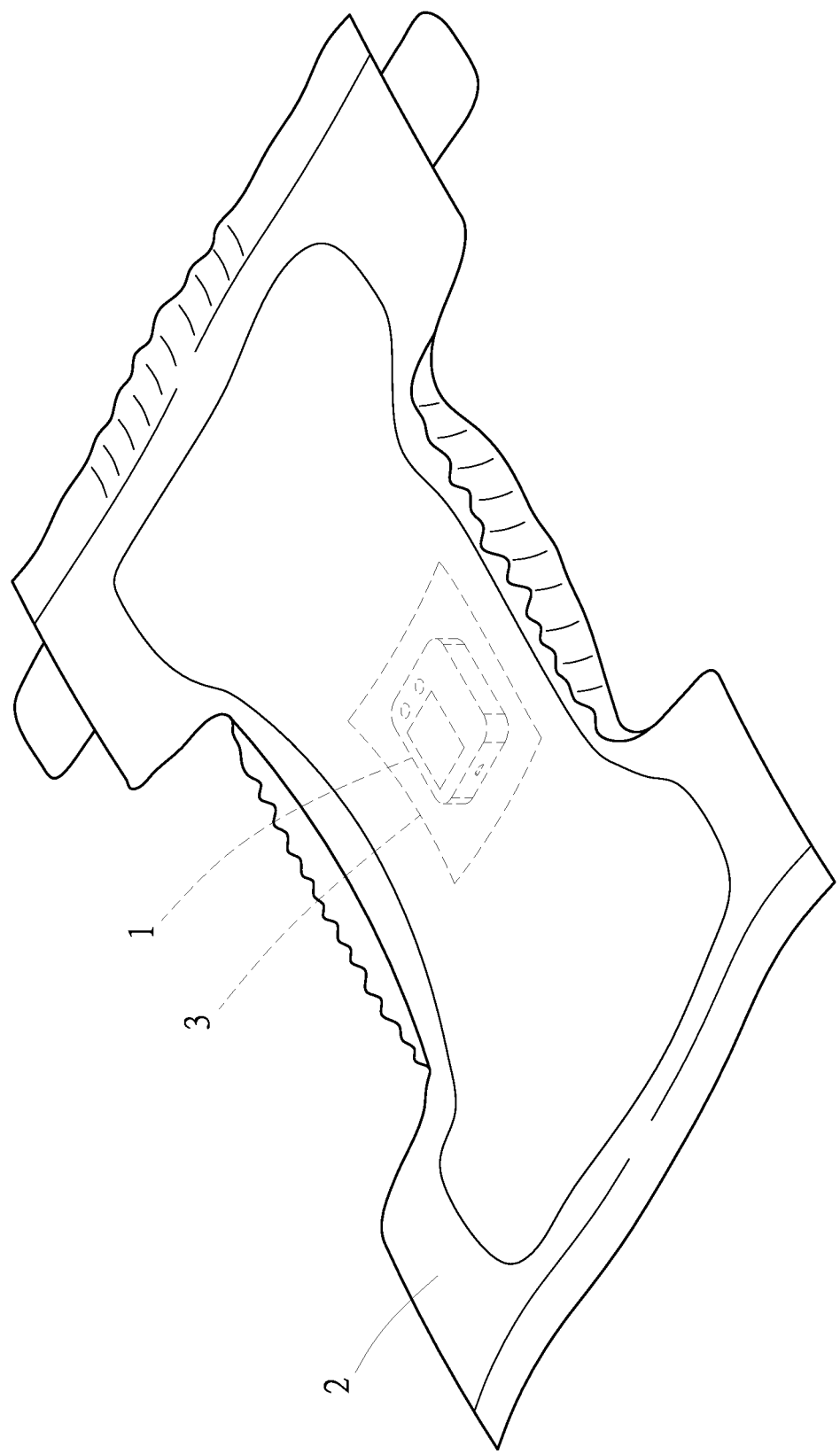
FIG. 3 is a schematic view, illustrating that the urine detection device of the present invention is attached to the diaper with the adhesive.

As shown in FIG. 1 through FIG. 3, a urine detection device of the present invention comprises a main body 1. The main body 1 includes a capacitive humidity detection unit 11, a processing unit 12, a reminder unit 13, a wireless transmission element 14, and a rechargeable battery module 15. The capacitive humidity detection unit 11 has a sensing electrode. The processing unit 12 is connected to the capacitive humidity detection unit 11. The reminder unit 13 is connected to the processing unit 12. The wireless transmission element 14 is connected to the processing unit 12. The rechargeable battery module 15 is connected to the capacitive humidity detection unit 11, the processing unit 12, the reminder unit 13, and the wireless transmission element 14. The wireless transmission element 14 is any one of a Bluetooth, a wireless network WI-FI, a near field communication NFC and a radio frequency identification RFID. The main body 1 is adhered to a diaper 2 with an adhesive 3. The adhesive 3 may be an aquogel or a double-sided tape.

Figure 4:
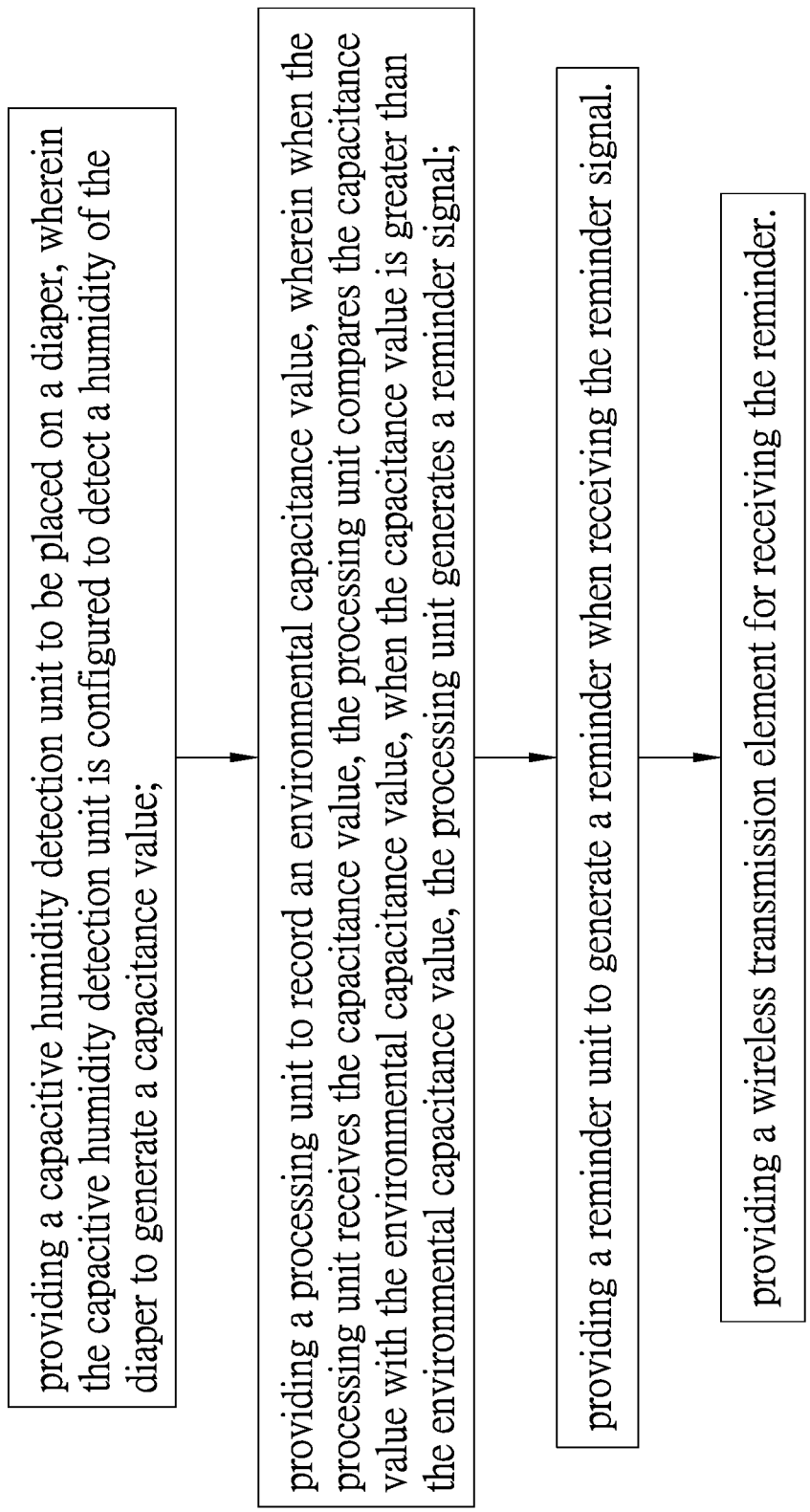
FIG. 4 is a flowchart of the urine detection method of the present invention.

As shown in FIG. 1 and FIG. 4, a urine detection method for the urine detection device of the present invention comprises the following steps. The man body 1 of the urine detection device is placed on the diaper 2, and the sensing electrode in the capacitive humidity detection unit 11 of the main body 1 detects the humidity of the diaper 2 to generate a capacitance value. The processing unit 12 records an environmental capacitance value. The environmental capacitance value can be preset for recording, or when the urine detection device is placed on the diaper 2, the capacitive humidity detection unit 11 starts to sense and record in the processing unit 12. That is, the environmental capacitance value can be adjusted with the environmental humidity. When the processing unit 12 receives the capacitance value, the processing unit 12 compares the received capacitance value with the environmental capacitance value. When the capacitance value is greater than the environmental capacitance value, the processing unit 12 generates a reminder signal. When the reminder unit 13 receives the reminder signal, it will generate a reminder. The reminder can be displayed on the main body 1 for screen display or/and a voice reminder. It is possible to receive the reminder through the wireless transmission element 14, and then the reminder is transmitted to a caregiver. It should be noted that the environmental capacitance value is the capacitance value before the humidity is detected by the sensing electrode.

Figure 5:
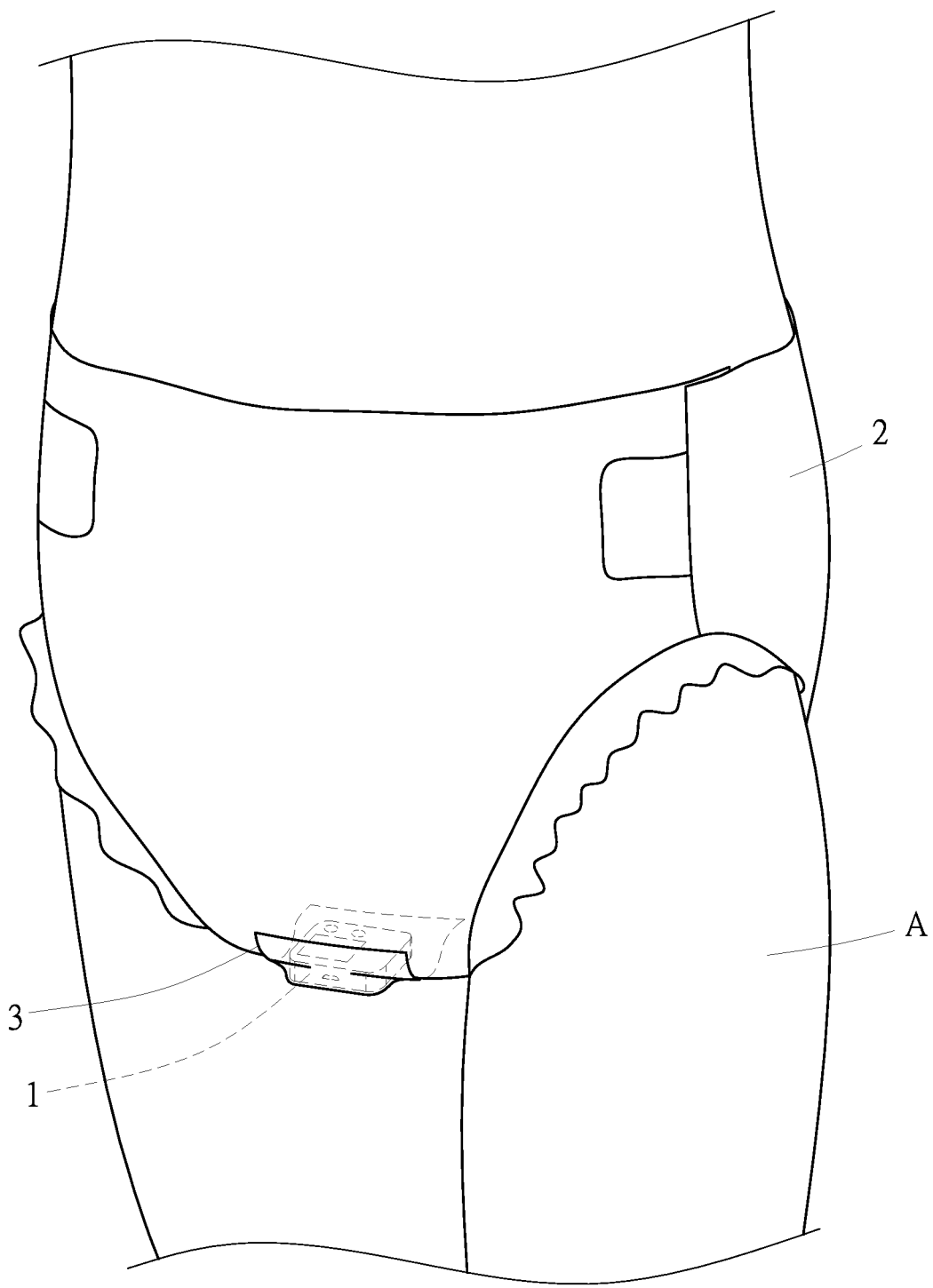
FIG. 5 is a schematic view showing the use of the urine detection device of the present invention.

Please refer to FIG. 1, FIG. 4 and FIG. 5. In this embodiment, a user A puts on the diaper 2. When the capacitive humidity detection unit 11 of the main body 1 senses the humidity of the diaper 2, the capacitance value is generated. The capacitance value is generated by the urine of the user A. The capacitive humidity detection unit 11 transmits the capacitance value to the processing unit 12. When the processing unit 12 receives the capacitance value, the processing unit 12 transmits the reminder signal to the reminder unit 13. The reminder unit 13 reminds the caregiver of the reminder. The reminder may be transmitted from the reminder unit 13 to the wireless transmission element 14, and the wireless transmission element 14 transmits the reminder to the caregiver. When the caregiver receives the reminder, he/she can judge whether the diaper 2 has urine through the received reminder, and then decide whether to change the diaper 2 or not. The adhesive 3 can be directly discarded and replaced. There is no need to clean the adhesive 3 for reuse. The main body 1 can be charged by the rechargeable battery module 15. There is no need to replace the battery. It can be charged and used repeatedly.

Figure 6:
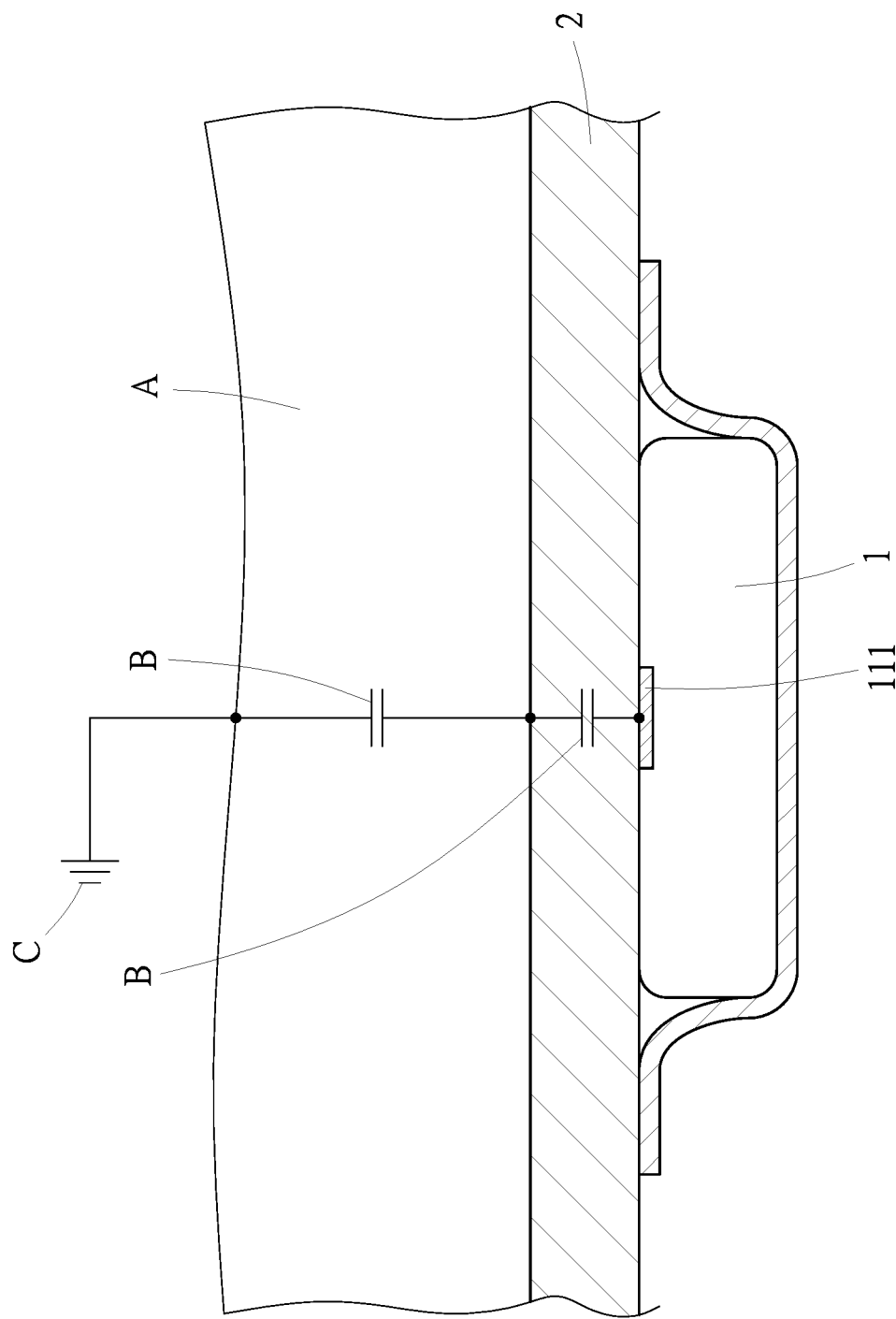
FIG. 6 is a schematic view, showing the sensing of the capacitive humidity detection unit of the present invention.
Figure 8:
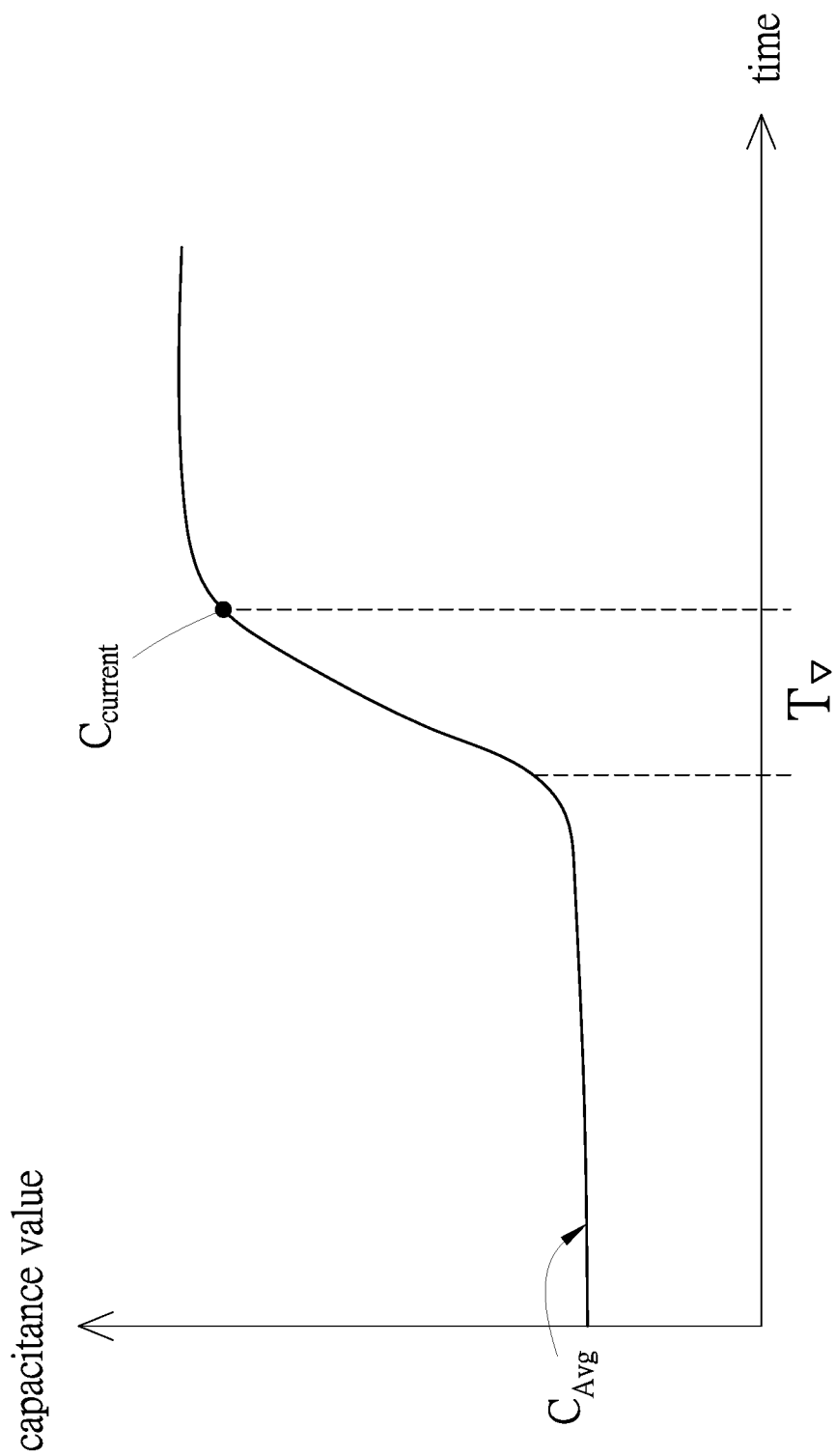
FIG. 8 is a graph of the relationship between the capacitance value and time of the present invention.

Referring to FIG. 6 and FIG. 8, the environmental capacitance value can be preset, or when the urine detection device is placed on the diaper 2, the capacitive humidity detection unit 11 is used to start sensing and the processing unit 12 records. The way the urine detection device is placed on the diaper 2 to start recording is described below. The diaper 2 has a parasitic capacitance B. The main body 1 has a sensing electrode 111. The environmental capacitance value is obtained by conducting the sensing electrode 111 through the parasitic capacitance B. The recording method of the environmental capacitance value is to record once every minute. An average capacitance value ($C_{Avg}$) is obtained by averaging the environmental capacitance values. A critical value of capacitance change is set. The critical value can be set to any value in the range of, for example, 15% to 40%, that is, it is preset that the user A puts on the diaper 2 and feels that the diaper 2 is wet but not too wet and uncomfortable. The critical value is equivalent to the formula of capacitance change as $$\frac{C_{current} - C_{Avg}}{C_{Avg}}.$$

After the user A puts on the diaper 2, the user A and the diaper each have a parasitic capacitance B, and the user A has a grounding point relative to the diaper 2. When the sensing electrode 111 senses a change in the current capacitance value (Ccurrent) and when the capacitance change of the current capacitance value (Ccurrent) is greater than the critical value, it is determined as a wet state.

Figure 7:
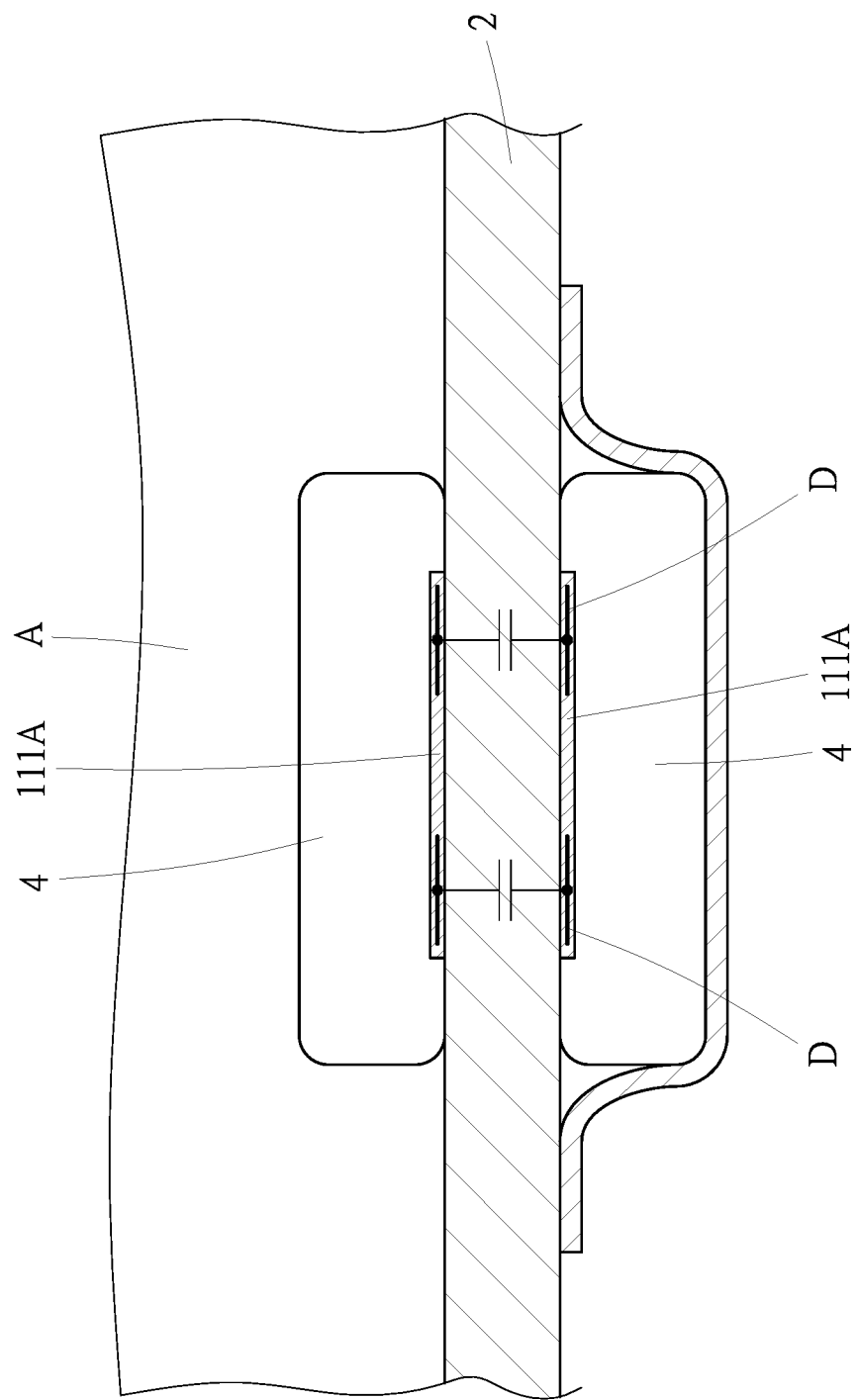
FIG. 7 is a schematic view, showing the humidity detection of the urine wetness sensing system as disclosed in Taiwan Patent Publication No. 1327063.

FIG. 7 illustrates the urine wetness sensing system 4 of the above-mentioned patent. The capacitance sensor and the electrode of the above-mentioned patent need to be equipped with two sensing electrodes 111A corresponding to the present invention. The sensing electrodes 111A detect the humidity by means of a single electrode D, so they need to be placed on the inside of the diaper 2A to be in contact with the user A and the outside of the diaper 2 respectively to perform a calculation by detecting the single electrode D on both sides of the user A and the diaper 2. However, the inner part may touch the user A and cause discomfort, and the production cost is relatively high.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A urine detection method, comprising the steps of:
providing a capacitive humidity detection unit placed on an external surface of a diaper, the capacitive humidity detection unit being devoid of contact with a user and having a sensing electrode, wherein the capacitive humidity detection unit is configured to detect a humidity of the diaper and generate a capacitance value responsive thereto, the capacitance value being based on a capacitance between the sensing electrode and the user;
providing a processing unit to record an environmental capacitance value, wherein when the processing unit receives the capacitance value, the processing unit compares the capacitance value with a preset critical capacitance value, when the capacitance value is greater than the preset critical capacitance value, the processing unit generates a reminder signal, wherein the environmental capacitance value is recorded once every minute, an average capacitance value is obtained by averaging the environmental capacitance values, and the preset critical capacitance value is 15 to 40% greater than the average capacitance value; and
providing a reminder unit to generate a reminder when receiving the reminder signal.

2. The urine detection method as claimed in claim 1, further providing a wireless transmission element for receiving the reminder.

3. A urine detection device, attached to a diaper to be put on a human body, comprising:
a main body;
a capacitive humidity detection unit disposed on the main body, having a sensing electrode, wherein when the main body is attached to an external surface of the diaper, and is devoid of contact with a human body, the sensing electrode forms a capacitance value with the human body;
a processing unit disposed on the main body, the processing unit being connected to the capacitive humidity detection unit and configured to record a preset critical capacitance value, wherein when the processing unit receives the capacitance value, the processing unit compares the capacitance value with the preset critical capacitance value, when the capacitance value is greater than the preset critical capacitance value, the processing unit generates a reminder signal, wherein an environmental capacitance value is recorded once every minute, an average capacitance value is obtained by averaging the environmental capacitance values, and the preset critical capacitance value is 15 to 40% greater than the average capacitance value; and
a reminder unit disposed on the main body, the reminder unit being connected to the processing unit, wherein when the reminder unit receives the reminder signal, the reminder unit generates a reminder.

4. The urine detection device as claimed in claim 3, further comprising a wireless transmission element disposed on the main body, the wireless transmission element being connected to the reminder unit, the wireless transmission element being configured to receive the reminder.

5. The urine detection device as claimed in claim 4, wherein the wireless transmission element is any one of a Bluetooth, a wireless network WI-FI, a near field communication NFC and a radio frequency identification RFID.

6. The urine detection device as claimed in claim 3, wherein the main body includes a rechargeable battery module, and the rechargeable battery module is connected to the capacitive humidity detection unit, the processing unit and the reminder unit.

7. The urine detection device as claimed in claim 3, further comprising an adhesive, wherein the main body is adhered to the diaper with the adhesive, and the adhesive is an aquogel or a double-sided tape.

* * * * *